United States Patent
Huang et al.

(10) Patent No.: US 10,792,317 B2
(45) Date of Patent: Oct. 6, 2020

(54) **METHOD FOR REDUCING BODY FAT BY ADMINISTERING *LACTOBACILLUS PLANTARUM***

(71) Applicants: SYNBIO TECH INC., Kaohsiung (TW); National Taiwan Sport University, Taoyuan (TW)

(72) Inventors: Chi-Chang Huang, Taoyuan (TW); Wen-Ching Huang, Taipei (TW); Jin-Sheng Lin, Kaohsiung (TW); Mon-Chien Lee, Taoyuan (TW); Ker-Sin Ng, Kaohsiung (TW)

(73) Assignees: SYNBIO TECH INC., Kaohsiung (TW); NATIONAL TAIWAN SPORT UNIVERSITY, Taoyuan (TW)

( * ) Notice: Subject to any disclaimer, the term of this patent is extended or adjusted under 35 U.S.C. 154(b) by 62 days.

(21) Appl. No.: 16/217,475

(22) Filed: Dec. 12, 2018

(65) Prior Publication Data
US 2019/0111091 A1    Apr. 18, 2019

Related U.S. Application Data

(63) Continuation-in-part of application No. 15/385,786, filed on Dec. 20, 2016, now Pat. No. 10,188,685.

(30) Foreign Application Priority Data

Aug. 24, 2016   (TW) .............................. 105126982 A

(51) Int. Cl.
| | |
|---|---|
| *A61K 35/747* | (2015.01) |
| *A23L 33/00* | (2016.01) |
| *A61K 9/00* | (2006.01) |
| *A61P 3/06* | (2006.01) |
| *A23L 33/135* | (2016.01) |

(52) U.S. Cl.
CPC .......... *A61K 35/747* (2013.01); *A23L 33/135* (2016.08); *A23L 33/30* (2016.08); *A61K 9/0053* (2013.01); *A61P 3/06* (2018.01); *A23V 2002/00* (2013.01); *A23Y 2220/67* (2013.01)

(58) Field of Classification Search
None
See application file for complete search history.

(56) References Cited

U.S. PATENT DOCUMENTS 10,463,704 B2 *  11/2019  O'Hara ................ A61K 35/747

* cited by examiner

*Primary Examiner* — Vera Afremova
(74) *Attorney, Agent, or Firm* — WPAT, PC

(57) ABSTRACT

The present invention is directed to a use of *Lactobacillus plantarum* LP10 for reducing body fat, controlling obesity or overweight, and alleviating an obesity-related disease caused by excessively high body fat. The *Lactobacillus plantarum* LP10 is deposited in China General Microbiological Culture Collection Center (CGMCC), the accession number is CGMCC 13008.

19 Claims, 3 Drawing Sheets

METHOD FOR REDUCING BODY FAT BY ADMINISTERING *LACTOBACILLUS PLANTARUM*

BACKGROUND OF THE INVENTION

This application is a continuation-in-part application of U.S. application Ser. No. 15/385,786 filed on Dec. 20, 2016.

BACKGROUND OF THE INVENTION

1. Field of the invention

The present invention relates to the field of probiotics, and more specifically to use of *Lactobacillus plantarum* for reducing body fat.

2. Description of the prior art

*Lactobacillus plantarum* is a gram-positive bacterium that can be found in fermented food or animal's saliva. It has the largest genome in lactic acid bacteria. Therefore, *Lactobacillus plantarum* has many variations and so has many applications.

Previously studies reported that *Lactobacillus plantarum* has many medical applications, including regulation of inflammation-related diseases, protection of viral infection in respiratory tracts, and increasing the sensitivity of cancer cells to the medicine mixed with *Lactobacillus plantarum*. In addition, *Lactobacillus plantarum* can be used for a variety of food additives. For example, it can be used to prevent the growth of poisonous fungi for corns.

Body fat is an adipose tissue of human or animal body. There are two types of body fat: visceral fat and subcutaneous fat. Visceral fat is a fat tissue that surrounds organs and subcutaneous fat is a fat tissue stored under the skin. Excess accumulation of body fat may cause obesity and overweight that increases the risk of various diseases such as cardiovascular diseases, diabetes, and cancer.

The common strategies on reducing obesity and overweight including diet, medical treatment, therapeutic operation, and exercise. However, diet, medical treatment, and therapeutic operation usually come with adverse effects. Exercise thus may be a better way to reduce obesity and overweight but the Cochrane Collaboration found that exercising alone got limited weight loss result.

In order to reduce obesity and overweight, it needs a natural substance that can reduce body fat without adverse effects, especially a natural substance that can be used in combination with exercise. The present applicant's prior application, U.S. application Ser. No. 15/385,786 addresses *Lactobacillus plantarum* LP10 can be used to improve exercise performance and mentions that epididymal fat pad (EFP), a kind of visceral fat, weight dose-dependently decreased with *Lactobacillus plantarum* LP10 supplementation. For the present, however, whether *Lactobacillus plantarum* LP10 can reduce whole body fat effectively is not yet reported.

SUMMARY OF THE INVENTION

The present invention provides a method for reducing body fat in an individual, comprising administering a therapeutically effective amount of a probiotic composition including *Lactobacillus plantarum* LP10 with the deposition number CGMCC13008.

In order to achieve the aforementioned objective, the reducing body fat comprises reducing subcutaneous fat.

In order to achieve the aforementioned objective, the reducing body fat comprises reducing visceral fat.

In order to achieve the aforementioned objective, the method is for reducing body fat after exercise.

In order to achieve the aforementioned objective, the therapeutically effective amount comprises an administrated dosage of the *Lactobacillus plantarum* LP10 being greater than or equal to $3\times10^{10}$ CPU (colony forming unit) per day.

In order to achieve the aforementioned objective, the *Lactobacillus plantarum* LP10 is selective from the group consisting of live *Lactobacillus plantarum* LP10 and dead *Lactobacillus plantarum* LP10.

In order to achieve the aforementioned objective, the composition is in a dosage form suitable for oral administration.

In order to achieve the aforementioned objective, the dosage form is selected from the group consisting of solutions, suspensions, emulsions, powders, tablets, pills, syrups, lozenges, troches, chewing gums, slurries and capsules.

In order to achieve the aforementioned objective, the probiotic composition further comprises pharmaceutically acceptable carrier, vehicle or thinner In order to achieve the aforementioned objective, the composition further comprises an edible material, the edible material comprises water, fluid milk product, milk, concentrated milk, fermented milk, yogurt, sour milk, frozen yogurt, lactic acid bacterial-fermented beverages, milk powder, ice cream, cream cheese, dry cheese, soybean milk, fermented soybean milk, vegetable-fruit juice, juice, sports drinks, confectioneries, jellies, candies, infant formulas, health foods, animal feeds, Chinese herbs or dietary supplements.

In order to achieve the aforementioned objective, the composition further comprises at least one of the probiotic bacteria strain selected from the group consisting of *Lactobacillus* sp., *Streptococcus* sp., *Bifidobacterium* sp., and yeasts.

The present invention also provides a method for controlling obesity or overweight in an individual, comprising administering a therapeutically effective amount of a probiotic composition including *Lactobacillus plantarum* LP10 with the deposition number CGMCC13008.

In order to achieve the aforementioned objective, the controlling obesity or overweight is achieved by reducing body fat.

In order to achieve the aforementioned objective, the *Lactobacillus plantarum* LP10 is selective from the group consisting of live *Lactobacillus plantarum* LP10 and dead *Lactobacillus plantarum* LP10.

In order to achieve the aforementioned objective, the therapeutically effective amount comprises an administrated dosage of the *Lactobacillus plantarum* LP10 being greater than or equal to $3\times10^{10}$ CPU (colony forming unit) per day.

The present invention further provides a method for alleviating, treating or preventing an obesity-related disease caused by excessively high body fat in an individual, comprising administering a therapeutically effective amount of a probiotic composition including *Lactobacillus plantarum* LP10 with the deposition number CGMCC13008.

In order to achieve the aforementioned objective, the obesity-related disease is cardiovascular disease, diabetes, or cancer.

In order to achieve the aforementioned objective, the alleviating, treating or preventing the obesity-related disease is achieved by controlling body fat.

In order to achieve the aforementioned objective, the *Lactobacillus plantarum* LP10 is selective from the group consisting of live *Lactobacillus plantarum* LP10 and dead *Lactobacillus plantarum* LP10.

The present invention demonstrates that both the *Lactobacillus plantarum* LP10 viable bacterium and the heat-killed bacteria group can reduce the body fat; moreover, it is a dose-dependent effect. *Lactobacillus plantarum* LP10 can be used to reduce body fat, control obesity and overweight, or improve the diseases and symptoms caused by excessively high body fat.

The advantages of the new uses of the probiotics provided in the present invention are as follows:

For the first time, *Lactobacillus plantarum* LP10 is provided for reducing the body fat without adverse effects and the effects are demonstrated by the rigorous human clinical data. *Lactobacillus plantarum* LP10 can be also used in combination with exercise; for athletes, it can help enhance physical functions in all aspects. Besides, body fat are the causes or evaluation factors of common diseases or symptoms so the uses of the probiotics in the present invention will help to improve the diseases and symptoms caused by excessively high body fat.

DETAILED DESCRIPTION OF THE PREFERRED EMBODIMENT

Figure 1:
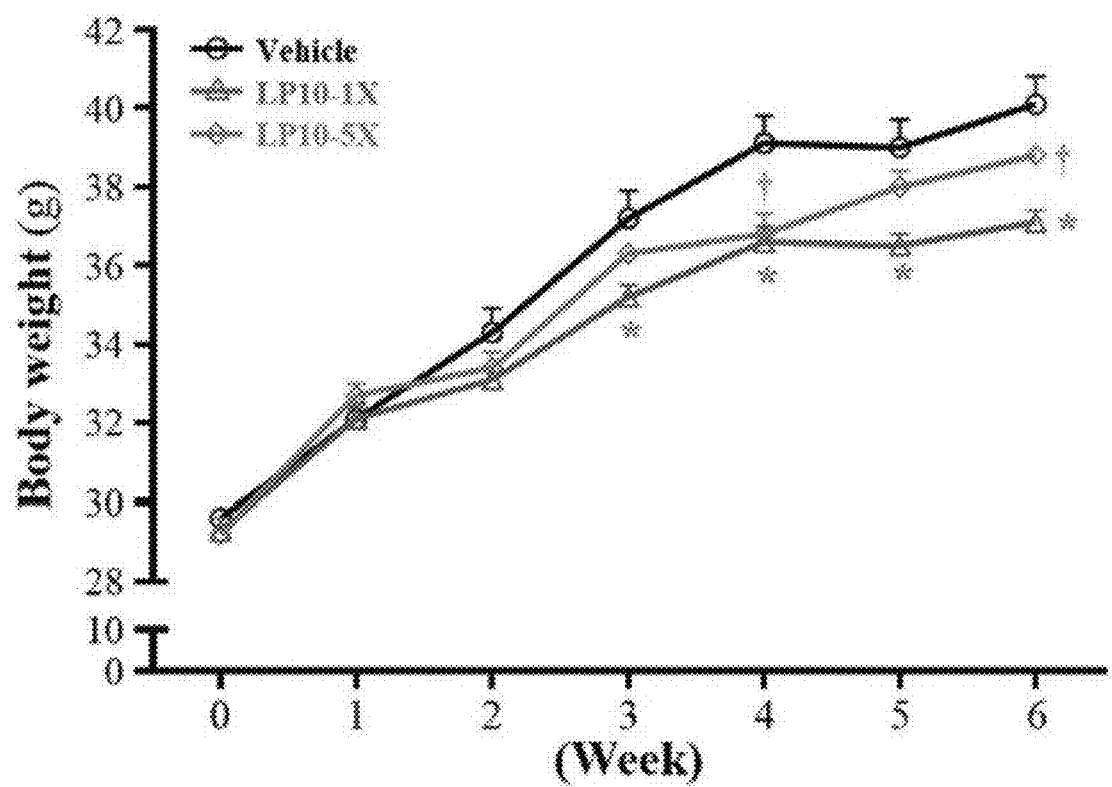
FIG. 1 shows the change in body weight (BW) during the experiment.

The technical features of the present invention, including specific features, are defined by the claims. For the technical features of the present invention, the understanding, preferably, should coordinate with the specification, the embodiment, the drawings and the detailed description.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

As used herein, the term "probiotics" refers to microorganisms that provide a physiological benefit to a user when given properly. The microorganisms have no toxicity, but intestinal adhesion and beneficial effects.

The term "carrier" or "vehicle" as used herein, refers to relatively nontoxic chemical compounds or agents that facilitate the incorporation of a compound into cells or tissues.

The foregoing may be aromatics, buffers, binders, colorants, disintegrants, diluents, emulsifiers, extenders, flavor-improving agents, gellants, glidants, antiseptics, skin-penetration enhancers, solubilizers, stabilizers, suspending agents, sweeteners, tonicity agents, viscosity-increasing agents, or any combination thereof.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like.

The term "maximal oxygen uptake (abbreviated as $VO_{2max}$)" refers to a highest value of oxygen that can be consumed or utilized by tissue cells when a person is engaged in the most intense exercise above sea level; the term "endurance exercise ability test with fixed intensity and time" refers to exercise testing on a treadmill or bicycle with an intensity of 60% $VO_{2max}$ or more for at least 30 minutes.

The appropriate routes of administration include, but not limited to, oral, intravenous, rectal, aerosol, parenteral, ocular, pulmonary, mucosal penetration through the skin, vaginal, otic, nasal, and topical.

In addition, examples of gastrointestinal administration include, but not limited to, intramuscular, subcutaneous, intravenous, intramedullary, and intramedullary, intraventricular, intraperitoneal, intra-lymph, intranasal.

The following treatment embodiments are illustrative only, due to the large variability of individual treatment sessions, and the deviation from the recommended value is not unusual. The dose may vary, depending on the variation, but not limited to the activity of the compound, the disease or physiological state of treatment, the mode of administration, individual needs, severity of the disease, and physician judgment.

The toxicity and efficacy of the treatment may be determined by standard pharmaceutical procedures for cell culture or animal testing, including but not limited to, determining the effective dose ($ED_{50}$, half the dose of therapeutic effect).

The probiotic composition used in the present invention; herein the probiotic may be active or inactive. Furthermore, the inactive probiotic can be heat inactivation or lyophilization.

The probiotic composition herein include, but not limited to, solutions, emulsions, suspensions, powders, tablets, pills, lozenge, troche, chewing gum, capsules, slurries, and other dosage forms similar or applicable to the present invention.

The probiotic composition herein may optionally include other strains as taught by a person having ordinary skill in the art.

The inventive composition may further include at least one of the following groups of known probiotic strains: *Lactobacillus* sp., *Streptococcus* sp., *Bifidobacterium* sp., and yeasts.

Furthermore, the known *Lactobacillus* sp. include, but are not limited to, *Lactobacillus lactis, Lactobacillus acidophilus, Lactobacillus helveticus, Lactobacillus bifidus, Lactobacillus casei, Lactobacillus paracasei* subsp. *paracasei, Lactobacillus rhamnosus, Lactobacillus gasseri, Lactobacillus reuteri* and *Lactobacillus fermentum* or their combinations thereof.

The known *Streptococcus* sp. include, but are not limited to, *Streptococcus lactis, Streptococcus thermophilus, Streptococcus cremoris* or their combinations thereof.

The known *Bifidobacterium* sp. include, but are not limited to, *Bifidobacterium breve, Bifidobacterium lactis, Bifidobacterium longum, Bifidobacterium bifidum* or their combinations thereof.

The known yeasts include, but are not limited to, *Saccharomyces cereviseae, Candida kefyr, Saccharomyces florentinus* or their combinations thereof.

The probiotic composition herein may be a food composition, further formulate as a capsule, lozenge, beverage, powder, or dairy product, optionally, other probiotics such as *Enterococcus, Bifidobacterium, Bacillus, Streptococcus* and *Lactococcus*.

The composition provided herein can be manufactured as a food product or health product by addition of an edible material. Said edible material includes, but is not limited to, water, fluid milk products, milk, concentrated milk, fermented milk, yogurt, sour milk, frozen yogurt, lactic acid bacteria-fermented beverages, milk powder, ice cream, cream cheese, dry cheese, soybean milk, fermented soybean milk, vegetable-fruit juices, juices, sports drinks, confectioneries, jellies, candies, infant formulas, health foods, animal feeds, Chinese herbs and dietary supplements.

The composition provided herein can be manufactured as a dietary supplement which may be administered to a user in admixture with a suitable drinkable liquid such as water, yoghurt, milk or fruit juice or may be mixed with a solid or liquid food product. The excipient included in the inventive composition consists of, but is not limited to, solution, suspension, emulsion, powder, tablet, pill, lozenge, troche, chewing gum, slurry and other similar or suitable dosage forms for use in the invention.

In the present embodiment of the invention, the therapeutical effective varies depending on the combination with different therapies. The combination therapy may further include a periodical treatment, referring to multiple initiation and cessation of treatments to assist in the clinical management of the patient. The description in the present specification regarding the combination treatment and the dose of co-administration are varied by the co-administered drug, the disease, the physiological abnormality, and the physiological condition.

In the present embodiment of the invention, in order to achieve the treatment, prevention, or amelioration of physiological conditions and symptoms, it is necessary to change and amend the medication administration according to a number of factors. The aforementioned factors include physiological abnormalities of patients, age, weight, sex, diet, drug usage. Therefore, in another embodiment, the dose of treatment can be widely changed and deviated from the first course of treatment.

*Lactobacillus plantarum* LP10 (also known as *Lactobacillus plantarum* TWK10, hereinafter called "LP10") strain has been deposited in China General Microbiological Culture Collection Center (CGMCC) with a deposited number as CGMCC No. 13008, on Sep. 13, 2016, also at Bioresource Collection and Research Center of Taiwan with a deposited number as BCRC No. 910734, on Jun. 30, 2016. Before testing, the bacterial strains were retrieved from frozen storage and cultured in MRS broth for 24 h at 37° C. Before supplementation, cells were centrifuged at 3000 g for 10 min and washed twice with phosphate buffered saline (PBS). Pellets were resuspended in PBS, pH 7.2.

Male ICR mice (6 weeks old) grown under specific pathogen-free conditions were purchased from BioLASCO (Yi-Lan, Taiwan). All mice were provided a standard laboratory diet (No. 5001; PMI Nutrition International, Brentwood, Mo., USA) and distilled water ad libitum and housed at 12-h light/12-h dark cycle at room temperature (22° C.±1° C.) and 50%-60% humidity.

All animal testing data are expressed as mean±SEM, n=8 mice/group. Statistical differences among groups were analyzed by a one-way analysis of variance (ANOVA) and the Cochran-Armitage test for the dose-effect trend analysis with SAS 9.0 (SAS Inst., Cary, N.C., USA). $p<0.05$ was considered statistically significant. Differences between groups were analyzed by one-way ANOVA using Duncan's post-hoc test, and p values<0.05 were considered significant.

Embodiment 1: General Characteristics of Mice with LP10 Supplementation for Six Weeks The human dose of LP10, $1 \times 10^{10}$ CFU, was modified from previous studies. The mouse LP10 dose ($2.05 \times 10^8$ CFU/kg) we used was converted from a human equivalent dose (HED) based on body surface area by the following formula from the US Food and Drug Administration: assuming a human weight of 60 kg, the HED for $1 \times 10^{10}$ colony-forming units (CFU)÷60 (kg)=$16.67 \times 10^{7 \times 12.3}$=a mouse dose of $2.05 \times 10^8$ CFU/kg; the conversion coefficient 12.3 was used to account for differences in body surface area between a mouse and a human.

In total, 24 mice were randomly assigned to 3 groups (8 mice/group) for daily oral LP10 treatment for 6 weeks: vehicle, $2.05 \times 10^8$ CFU/kg (LP10-1X), and $1.03 \times 10^9$ CFU/kg (LP10-5X). The vehicle group received the same volume of solution equivalent to individual body weight (BW).

After LP10 supplement for six weeks, all mice were euthanized with 95% $CO_2$ asphyxiation. Initial BW did not differ among the vehicle, LP10-1X, and LP10-5X groups (Table 1). After six-week supplementation with LP10, the final BW was lower with LP10-1X and LP10-5X, by 7.47% (p=0.0003) and 3.46% (p=0.0567), respectively, than with vehicle treatment. In addition, daily intake of diet and water increased in LP10-5X fed mice. Trend analysis showed that daily intake of diet (p<0.0001) and water (p<0.0001) dose-dependently increased with LP10 supplementation, so daily diet intake was increased but BW was decreased. In addition, BW was significantly lower (p<0.05) with vehicle treatment at Week 3 of LP10 supplementation (FIG. 1).

Thus, three-week LP10 supplementation may change the body composition and energy utilization.

We measured the effect of LP10 on the muscle and epididymal fat pad (EFP) mass and relative tissue weight (different tissue weights adjusted for individual BW %). The EFP weight was lower by 34.62% (p=0.003) and 50.30% (p<0.0001) with LP10-1X and LP10-5X, respectively, than with vehicle treatment. Trend analysis showed that EFP weight dose-dependently decreased with LP10 supplementation (p<0.0001). The relative weight of EFP (%) was lower by 28.93% (p=0.0048) and 48.22% (p<0.0001) with LP10-1X and LP10-5X, respectively, than with vehicle treatment.

The relative weight (%) of muscle (gastrocnemius and soleus muscles) was greater by 1.10 (p=0.0003) and 1.07 folds (p=0.0098) with LP10-1X and LP10-5X, respectively, than with vehicle treatment. Trend analysis also showed a significant dose-dependent decrease and increase in relative EFP weight (%) and relative muscle weight (%), respectively, with LP10 supplementation. Thus, supplementation of LP10 for six weeks could change body composition to more fit and stronger. In addition, trend analysis showed significant increases in relative weight (%) of the kidney (p<0.0001) and heart (p=0.0018) with increasing LP10 dose. We found no gross abnormalities attributed to LP10 when weighing organs.

TABLE 2

Biochemical analysis with LP10 supplementation at the end of the experiment.

| Variable | Vehicle | LP10-1X | LP10-5X | Trend Analysis |
|---|---|---|---|---|
| CK (U/L) | 193 ± 36 | 169 ± 22 | 181 ± 25 | 0.8469 |
| TP (g/dL) | 4.8 ± 0.1 | 4.9 ± 0.1 | 4.9 ± 0.1 | 0.9571 |
| Albumin (g/dL) | 3.6 ± 0.0 [b] | 3.6 ± 0.0 [b] | 3.3 ± 0.1 [a] | 0.012 (↓) |
| BUN (mg/dL) | 26.5 ± 0.5 [b] | 22.4 ± 0.6 [a] | 23.0 ± 0.9 [a] | 0.0017 (↓) |
| Creatinine (mg/dL) | 0.27 ± 0.01 | 0.27 ± 0.01 | 0.29 ± 0.01 | 0.4627 |
| UA (mg/dL) | 0.91 ± 0.03 | 1.01 ± 0.10 | 1.03 ± 0.10 | 0.5858 |
| TC (mg/dL) | 143 ± 6 | 144 ± 6 | 130 ± 3 | 0.1804 |
| TG (mg/dL) | 205 ± 12 [b] | 159 ± 11 [a] | 151 ± 6 [a] | 0.0005 |
| Glucose (mg/dL) | 166 ± 4 | 161 ± 5 | 157 ± 5 | 0.1336 |

Data are mean ± SEM, n = 8 mice/group.
Different letters ([a], [b]) in the same row indicate a significant difference at $p < 0.05$ by one-way ANOVA.
CK, creatine kinase; TP, total protein; BUN, blood urea nitrogen; UA, uric acid; TC, total cholesterol; TG, triacylglycerols.

Levels of biochemical indices, including CK, TP, creatinine, UA, TC, and glucose, did not differ among groups (p>0.05, Table 2). Serum albumin levels were lower by 7.64% (p=0.0375) with LP10-5X than with vehicle treat-

TABLE 1

General characteristics of mice with LP10 supplementation.

| Characteristics | Vehicle | LP10-1X | LP10-5X | Trend analysis |
|---|---|---|---|---|
| Initial BW (g) | 29.6 ± 0.2 | 29.3 ± 0.3 | 29.2 ± 1.2 | 0.5370 |
| Final BW (g) | 40.1 ± 0.7 [c] | 37.1 ± 0.3 [a] | 38.8 ± 0.1 [a, b] | 0.6493 |
| Food intake (g/day) | 6.3 ± 0.1 [a] | 6.2 ± 0.0 [a] | 7.5 ± 0.1 [b] | <0.0001 (↑) |
| Water intake (mL/day) | 6.9 ± 0.1 [a] | 6.8 ± 0.2 [a] | 7.6 ± 0.0 [b] | <0.0001 (↑) |
| weight (g) | | | | |
| Liver (g) | 2.13 ± 0.05 | 2.10 ± 0.05 | 2.10 ± 0.03 | 0.9075 |
| Kidney (g) | 0.68 ± 0.02 | 0.67 ± 0.04 | 0.72 ± 0.04 | 0.1272 |
| EFP (g) | 0.85 ± 0.07 [b] | 0.55 ± 0.03 [a] | 0.42 ± 0.05 [a] | <0.0001 (↓) |
| Heart (g) | 0.20 ± 0.01 | 0.20 ± 0.01 | 0.20 ± 0.00 | 0.3908 |
| Lung (g) | 0.21 ± 0.01 | 0.22 ± 0.01 | 0.21 ± 0.00 | 0.9353 |
| Muscle (g) | 0.36 ± 0.01 | 0.37 ± 0.01 | 0.37 ± 0.01 | 0.4790 |
| BAT (g) | 0.13 ± 0.01 | 0.12 ± 0.00 | 0.13 ± 0.01 | 0.9473 |
| Relative weight (%) | | | | |
| Liver | 5.29 ± 0.03 [a] | 5.65 ± 0.09 [b] | 5.43 ± 0.06 [a] | 0.1073 |
| Kidney | 1.70 ± 0.02 [a] | 1.81 ± 0.02 [b] | 1.86 ± 0.03 [b] | <0.0001 (↑) |
| EFP | 2.09 ± 0.16 [c] | 1.48 ± 0.09 [b] | 1.08 ± 0.15 [a] | <0.0001 (↓) |
| Heart | 0.49 ± 0.10 [a] | 0.54 ± 0.07 [b] | 0.53 ± 0.07 [b] | 0.0018 (↑) |
| Lung | 0.53 ± 0.03 [a] | 0.58 ± 0.03 [b] | 0.55 ± 0.01 [ab] | 0.2009 |
| Muscle | 0.90 ± 0.02 [a] | 0.99 ± 0.01 [b] | 0.96 ± 0.02 [b] | 0.0326 (↑) |
| BAT | 0.31 ± 0.01 | 0.31 ± 0.01 | 0.33 ± 0.02 | 0.6881 |

Data are mean ± SEM, n = 8 mice/group.
Different letters ([a], [b], [c]) in the same row indicate a significant difference at $p < 0.05$.
Food efficiency ratio: body weight (BW) gain (g/day)/food intake (g/day).
Muscle mass includes both gastrocnemius and soleus muscles in the back part of the lower legs.
BAT: brown adipose tissue; EFP: epididymal fat pad.
Mice were pretreated with vehicle, LP10-1X, or LP10-5X for six weeks.

Embodiment 2: Effect of LP10 Supplementation on Biochemical Variables at the End of the Experiment We further investigated whether six-week LP10 treatment affected other biochemical markers in healthy mice. We examined tissue- and health status-related biochemical variables and major organs including skeletal muscle, heart, kidney, and lung (Table 2).

ment. Serum BUN levels were lower by 15.50% (p=0.0218) and 13.29% (p=0.0037) with LP10-1X and LP10-5X, respectively, than with vehicle treatment. On trend analysis, serum albumin (p=0.0012) and BUN (p=0.0017) levels were dose-dependently decreased with LP10 supplementation. Therefore, long-term daily supplementation with LP10 may have potential for tissue protection and renal benefits.

In addition, serum level of TC, an index of lipid profile, was lower by 22.76% (p=0.0069) and 26.60% (p=0.0021) with LP10-1X and LP10-5X, respectively, than with vehicle treatment. Trend analysis showed significantly decreased serum TG levels (p=0.0005) with increasing LP10 dose.

Figure 2:
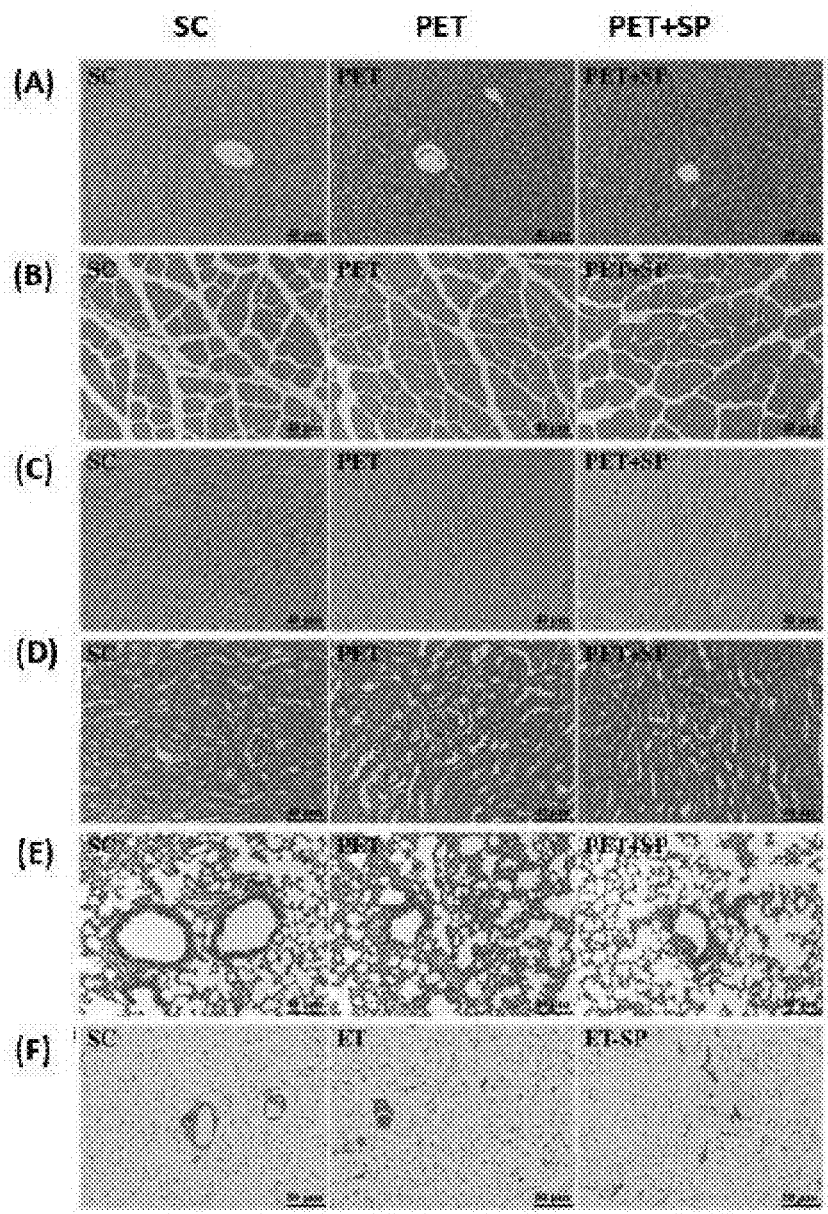
FIG. 2 shows the effect of *Lactobacillus plantarum* LP10 supplementation on morphology of: liver, skeletal muscle, heart, kidney, lungs, and epididymal fat pad.

All tissues were carefully removed, minced, and fixed in 10% formalin after sacrifice. Samples were embedded in paraffin and cut into 4-μm thick slices for morphological and pathological evaluations. Tissue was stained with hematoxylin and eosin (H & E) and examined under a light microscope equipped with a CCD camera (BX-51, Olympus, Tokyo, Japan) by a veterinary pathologist. LP10 supplementation for six weeks had no adverse effects on major organs such as the liver (FIG. 2a), skeletal muscle (FIG. 2b), heart (FIG. 2c), kidney (FIG. 2d), lung (FIG. 2e), and EFP (epididymal fat pad, FIG. 2f). Therefore, the dose of LP10 supplementation used in this study was safe.

Embodiment 3: Effects of the *Lactobacillus plantarum* LP10 on Reducing Body Fat The experiment employs a double-blind cross-over trial. The testees were between 20-40 years old. After two weeks of washout period and one week rest, each testee was given an administration of the probiotics for six weeks. The testees performing an endurance exercise test with fixed intensity at the beginning and end of the administration were divided into 5 groups according to a maximum oxygen uptake (VO$_{2max}$, mL/kg/min), 16 people in each group, and changes in the whole body fat were measured; the probiotic composition of each group was taken three times a day, one capsule at a time, and a dose of the administration and strain of each group are listed as follows:

(1) Placebo group: LP10-free placebo capsules (containing maltodextrin, lactose, microcrystalline α-cellulose), 3 capsules a day, take one capsule after each of three meals with warm water.
(2) Low-dose group-recommended 1 time dose of LP10 live bacteria group (LP10-L): One LP10 capsule containing 1×10$^{10}$ CFU, 3 capsules per day, 3×10$^{10}$ CFU/day, take one capsule after each of three meals with warm water.
(3) Middle-dose group-recommended 3 times dose of LP10 live bacteria group (LP10-M): One LP10 capsule containing 3×10$^{10}$ CFU, 3 capsules per day, 9×10$^{10}$ CPU/day, take one capsule after each of three meals with warm water.
(4) High-dose group-recommended 10 times dose of LP10 live bacteria group (LP10-H): One LP10 capsule containing 1×10$^{11}$ CFU, 3 capsules per day, 3×10$^{11}$ CFU/day, take one capsule after each of three meals with warm water.
(5) LP10 heat-killed bacteria group (LP10-HK): One LP10 heat-killed bacteria capsule containing 1×10$^{11}$ CFU, 3 capsules per day, 3×10$^{11}$ CFU/day, take one capsule after each of three meals with warm water.

Figure 3:
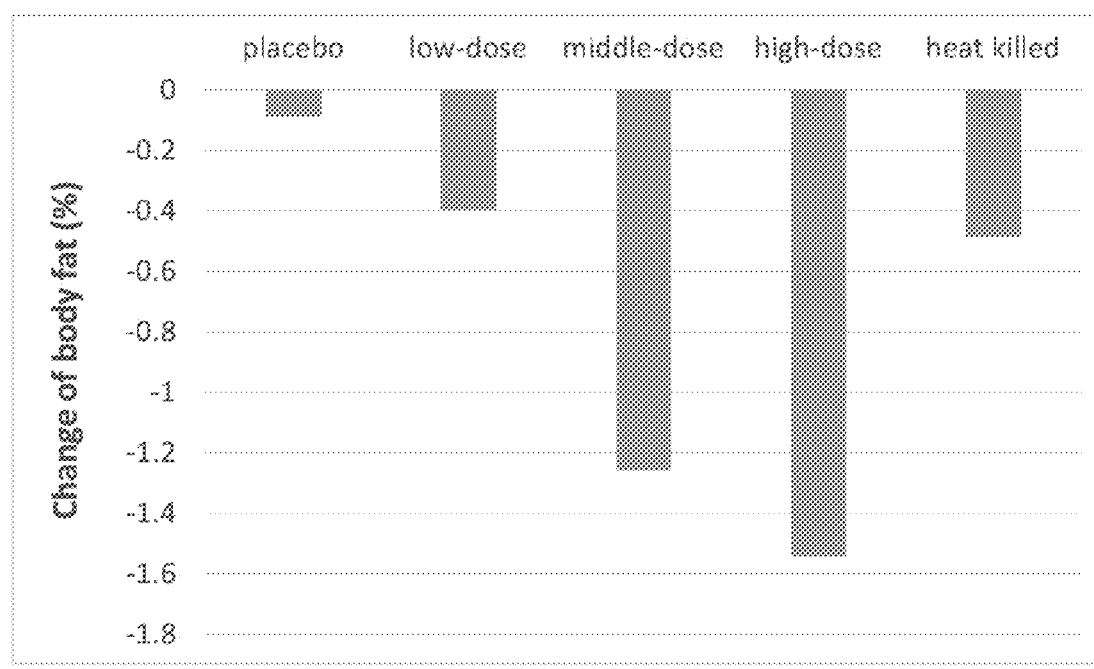
FIG. 3 shows changes in body fat after exercise and administration of the probiotic composition containing *Lactobacillus plantarum* LP10.

After taking the probiotic composition for six weeks, changes in body fat were analyzed after each of the testees had performed the endurance exercise test with fixed intensity and time. The results are shown in FIG. 3; the vertical axis indicates changes of body fat percentages measured at the end of the administration relative to the start of the administration.

The results show that both the live bacteria and heat-killed bacteria groups can reduce body fat, among them, the low-dose and heat-killed bacteria groups decreased by about 0.5% compared with the control group. As the dose increases, the body fat declines more significantly in the live bacteria group, and the high-dose group can make body fat decreased by 1.5%, indicating that LP10 has the effect of reducing body fat, whether it is in the form of live or non-activated bacteria.

In summary, LP10 has the effects of reducing body fat. Since excessively high body fat is one of the causes of systemic chronic inflammation, chronic diseases, cardiovascular diseases, diabetes, and cancer etc., implementation of any use of the results of the present invention to improve related diseases or symptoms caused by excessively high body fat, shall be deemed to be included in the scope of the claims of the present invention.

The above-mentioned detailed description aims to specifically illustrate the practicable embodiments of the present invention, but the embodiments are not for limiting the patent scope of the present invention and all equivalent embodiments or modifications made without departing from the spirit of the present invention shall be contained within the patent scope of the present invention.

The above-mentioned effects meet the lawful patent requirement for novelty and inventiveness. The inventor files an application according to law and earnestly urge honorable Office to approve the patent application of the present invention as an encouragement thereof.

What is claimed is:

1. A method for reducing body fat in an individual, comprising administering a therapeutically effective amount of a probiotic composition including *Lactobacillus plantarum* LP10 with the deposition number CGMCC13008; wherein the individual suffers from an excess of body fat.

2. The method of claim 1, wherein the reducing body fat comprises reducing subcutaneous fat.

3. The method of claim 1, wherein the reducing body fat comprises reducing visceral fat.

4. The method of claim 1, wherein the method is for reducing body fat after exercise.

5. The method of claim 1, wherein the therapeutically effective amount comprises an administrated dosage of the *Lactobacillus plantarum* LP10 being greater than or equal to 3×10$^{10}$ CFU (colony forming unit) per day.

6. The method of claim 1, wherein the Lactobacillus plantarum LP10 is selected from the group consisting of live *Lactobacillus plantarum* LP10 and dead *Lactobacillus plantarum* LP10.

7. The method of claim 1, wherein the composition is in a dosage form suitable for oral administration.

8. The method of claim 7, wherein the dosage form is selected from the group consisting of solutions, suspensions, emulsions, powders, tablets, pills, syrups, lozenges, troches, chewing gums, slurries and capsules.

9. The method of claim 1, wherein the probiotic composition further comprises pharmaceutically acceptable carrier, vehicle or thinner.

10. The method of claim 1, wherein the composition further comprises an edible material, the edible material comprises water, fluid milk product, milk, concentrated milk, fermented milk, yogurt, sour milk, frozen yogurt, lactic acid bacterial-fermented beverages, milk powder, ice cream, cream cheese, dry cheese, soybean milk, fermented soybean milk, vegetable-fruit juice, juice, sports drinks, confectioneries, jellies, candies, infant formulas, health foods, animal feeds, Chinese herbs or dietary supplements.

11. The method of claim 1, wherein the composition further comprises at least one of the probiotic bacteria strain selected from the group consisting of *Lactobacillus* sp., *Streptococcus* sp., *Bifidobacterium* sp., and yeasts.

12. A method for controlling obesity or overweight in an individual, comprising administering a therapeutically effective amount of a probiotic composition including *Lactobacillus plantarum* LP10 with the deposition number CGMCC13008; wherein the controlling obesity or overweight is achieved by reducing body fat; wherein the individual suffers from an excess of body fat.

13. The method of claim 12, within the controlling obesity or overweight is achieved by reducing triacylglycerols serum levels.

14. The method of claim 12, wherein the *Lactobacillus plantarum* LP10 is selected from the group consisting of live *Lactobacillus plantarum* LP10 and dead *Lactobacillus plantarum* LP10.

15. The method of claim 12, wherein the therapeutically effective amount comprises an administrated dosage of the Lactobacillus plantarum LP10 being greater than or equal to $3 \times 10^{10}$ CFU (colony forming unit) per day.

16. A method for alleviating, treating or preventing an obesity-related disease caused by excessively high body fat in an individual, comprising administering a therapeutically effective amount of a probiotic composition including *Lactobacillus plantarum* LP10 with the deposition number CGMCC13008; wherein the alleviating, treating or preventing the obesity-related disease is achieved by controlling body fat: wherein the individual suffers from an excess of body fat.

17. The method of claim 16, within the obesity-related disease is cardiovascular disease, or diabetes.

18. The method of claim 16, within the alleviating, treating or preventing the obesity-related disease is achieved by reducing triacylglycerols serum levels.

19. The method of claim 16, wherein the *Lactobacillus plantarum* LP10 is selected from the group consisting of live *Lactobacillus plantarum* LP10 and dead *Lactobacillus plantarum* LP10.

* * * * *